US010881597B2

(12) United States Patent
Lane et al.

(10) Patent No.: US 10,881,597 B2
(45) Date of Patent: Jan. 5, 2021

(54) COMPOSITIONS WITH SCALP HEALTH AGENTS WITH INCREASED DEPOSITION

(71) Applicant: The Procter & Gamble Company, Cincinnati, OH (US)

(72) Inventors: Brandon Scott Lane, Hamilton, OH (US); Eric Scott Johnson, Hamilton, OH (US); James Anthony Staudigel, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 15/976,485

(22) Filed: May 10, 2018

(65) Prior Publication Data
US 2018/0325791 A1    Nov. 15, 2018

Related U.S. Application Data

(60) Provisional application No. 62/505,551, filed on May 12, 2017.

(51) Int. Cl.
| A61K 8/02 | (2006.01) |
| A61Q 5/12 | (2006.01) |
| A61K 8/04 | (2006.01) |
| A61Q 5/02 | (2006.01) |
| A61K 8/58 | (2006.01) |
| A61Q 5/00 | (2006.01) |
| A61K 8/73 | (2006.01) |
| A61K 8/49 | (2006.01) |
| A61K 8/89 | (2006.01) |
| A61K 8/365 | (2006.01) |
| A61K 8/27 | (2006.01) |

(52) U.S. Cl.
CPC .............. *A61K 8/58* (2013.01); *A61K 8/0216* (2013.01); *A61K 8/0241* (2013.01); *A61K 8/046* (2013.01); *A61K 8/27* (2013.01); *A61K 8/365* (2013.01); *A61K 8/4913* (2013.01); *A61K 8/4926* (2013.01); *A61K 8/4933* (2013.01); *A61K 8/731* (2013.01); *A61K 8/737* (2013.01); *A61K 8/89* (2013.01); *A61Q 5/006* (2013.01); *A61Q 5/02* (2013.01); *A61Q 5/12* (2013.01); *A61K 2800/58* (2013.01); *A61K 2800/596* (2013.01)

(58) Field of Classification Search
None
See application file for complete search history.

(56) References Cited

U.S. PATENT DOCUMENTS

| 4,796,812 | A | * | 1/1989 | Grollier | ................. | A61K 8/046 |
| | | | | | | 239/303 |
| 6,060,044 | A | * | 5/2000 | Cretois | .................. | A61K 8/737 |
| | | | | | | 424/70.12 |
| 8,360,973 | B2 | | 1/2013 | Bazin | | |
| 9,996,674 | B2 | | 6/2018 | Segman | | |
| 10,543,157 | B2 | | 1/2020 | Davis | | |
| 2002/0150287 | A1 | | 10/2002 | Kobayashi | | |
| 2002/0183988 | A1 | | 12/2002 | Skaanning | | |
| 2003/0215522 | A1 | * | 11/2003 | Johnson | ................... | A61K 8/27 |
| | | | | | | 424/642 |
| 2004/0213751 | A1 | | 10/2004 | Schwartz | | |
| 2009/0274642 | A1 | | 11/2009 | Dawson, Jr. | | |
| 2010/0106679 | A1 | | 4/2010 | Yamaguchi | | |
| 2012/0309733 | A1 | | 12/2012 | Chang et al. | | |
| 2014/0028822 | A1 | | 1/2014 | Khadavi | | |
| 2014/0071456 | A1 | | 3/2014 | Podoleanu et al. | | |
| 2014/0120048 | A1 | | 5/2014 | Krueger | | |
| 2014/0171471 | A1 | | 6/2014 | Krueger | | |
| 2014/0378810 | A1 | | 12/2014 | Davis | | |
| 2015/0217465 | A1 | | 8/2015 | Krenik | | |
| 2015/0272865 | A1 | | 10/2015 | Mette | | |
| 2016/0038397 | A1 | | 2/2016 | Markland | | |
| 2016/0310393 | A1 | | 10/2016 | Chang | | |
| 2016/0346184 | A1 | | 12/2016 | Schwartz | | |
| 2017/0135932 | A1 | | 5/2017 | Schwartz | | |
| 2017/0270593 | A1 | | 9/2017 | Sherman | | |
| 2017/0367963 | A1 | | 12/2017 | Kadir | | |
| 2018/0040052 | A1 | | 2/2018 | Robinson | | |
| 2018/0225673 | A1 | | 8/2018 | Dubey | | |
| 2019/0035149 | A1 | | 1/2019 | Chen | | |

(Continued)

FOREIGN PATENT DOCUMENTS

| DE | 102012203240 A1 | 3/2013 |
| DE | 202015002188 U1 | 5/2015 |

(Continued)

OTHER PUBLICATIONS

U.S. Appl. No. 16/441,749, filed Jun. 14, 2019, Purwar et al.
U.S. Appl. No. 16/412,745, filed May 15, 2019, Schwartz et al.
U.S. Appl. No. 16/413,920, filed May 16, 2019, Niebauer et al.
All final and non-final office actions for U.S. Appl. No. 16/412,745.
All final and non-final office actions for U.S. Appl. No. 16/441,749.
All final and non-final office actions for U.S. Appl. No. 16/413,920.

(Continued)

*Primary Examiner* — Melissa S Mercier
(74) *Attorney, Agent, or Firm* — Linda M. Sivik

(57) ABSTRACT

A hair care composition having from about 10% to about 25% of one or more surfactants; from about 0.01% to 10% of one or more particulate scalp health agents; from about 0.01% to 10% of one or more surfactant soluble scalp health agents; from about 0.01% to 5% of one or more cationic polymers selected from the group consisting of a cationic cellulose; from about 0.01% to 5% of one or more cationic polymers selected from group consisting of one or more cationic guar polymers; and wherein an on-scalp deposition of the particulate scalp health agent deposition efficiency is increased by about 50% compared to a control with no soluble scalp health agent.

44 Claims, No Drawings

(56) References Cited

U.S. PATENT DOCUMENTS

| | | |
|---|---|---|
| 2019/0350514 A1 | 11/2019 | Purwar |
| 2019/0350819 A1 | 11/2019 | Hamersky |
| 2019/0355115 A1 | 11/2019 | Niebauer |
| 2020/0214953 A1 | 7/2020 | Lane |

FOREIGN PATENT DOCUMENTS

| | | | |
|---|---|---|---|
| WO | WO-9939683 A1 * | 8/1999 | ............... A61K 8/34 |
| WO | WO2012058557 A2 | 5/2012 | |
| WO | 2014073456 A1 | 5/2014 | |
| WO | 2014208162 A1 | 12/2014 | |

OTHER PUBLICATIONS

PCT International Search Report and Written Opinion for PC/US2018/032046 dated Jun. 27, 2018.

Schwartz, J.R. et al., "The role of oxidative damage in poor scalp health: ramifications to causality and associated hair growth", International Journal of Cosmetic Science, vol. 37, No. Suppl. 2, Sp. Iss. SI, Dec. 2015, pp. 9-15.

PCT International Search Report and Written Opinion for PCT/US2019/032382 dated Jul. 31, 2019.

PCT International Search Report and Written Opinion for PCT/US2019/032402 dated Aug. 28, 2019.

PCT International Search Report and Written Opinion for PCT/US2019/032404 dated Jul. 30, 2019.

"Anti-Dandruff Treatment Hair Cream", Mintel, Sep. 3, 2018.

"Balancing and Anti-Dandruff Shampoo", Mintel, Jan. 6, 2014.

"Double Care Anti-Dandruff Treatment Hair Cream", Mintel, Oct. 16, 2012.

"Hair Lotion", Mintel, Oct. 7, 2019.

"Moist-Up Eye Cream", Mintel, Nov. 11, 2009.

"Moisturizing Anti-Dandruff Shampoo", Mintel, Mar. 17, 2016.

PCT International Search Report and Written Opinion for PCT/US2019/066785 dated Mar. 26, 2020.

* cited by examiner

COMPOSITIONS WITH SCALP HEALTH AGENTS WITH INCREASED DEPOSITION

FIELD OF THE INVENTION

The present invention is directed to hair care compositions where it has been found that the addition of certain cationic polymers in combination with a particulate scalp health agent and surfactant soluble scalp health agent provide an unexpected increase in deposition benefits.

BACKGROUND OF THE INVENTION

For years, scalp health shampoos have been widely used to treat dandruff and clean hair and scalp, but there still remains a need for improved scalp health shampoos. In general, scalp health shampoos are formulated with scalp health agents in combination with surfactants and aqueous systems that are intended to deposit the scalp health agents on the scalp. The scalp health agents can be insoluble particulates such as zinc pyrithione and/or surfactant soluble substances such as climbazole or octopirox.

It has been surprisingly found that when combining multiple scalp health agents in a single formulation, one being soluble in the formula matrix and one in an insoluble particulate form, there is a synergistic increase in the amount of deposition of the particulates actives on the scalp Conventional wisdom would dictate that enhancing said active deposition is a key lever in driving greater efficacy from rinse off, scalp health treatment shampoos. Additionally, we have found that the degree of this enhanced deposition can be manipulated by the choice and level of the selected cationic polymers in the formula.

SUMMARY OF THE INVENTION

In an embodiment of the present invention, a hair care composition is comprising from about 10% to about 25% of one or more surfactants; from about 0.01% to 10% of one or more particulate scalp health agents; from about 0.01% to 10% of one or more surfactant soluble scalp health agents; from about 0.01% to 5% of one or more cationic polymers selected from the group consisting of a cationic cellulose; from about 0.01% to 5% of one or more cationic polymers selected from group consisting of one or more cationic guar polymers; and wherein an on-scalp deposition of the particulate scalp health agent deposition efficiency is increased by about 50% compared to a control with no soluble scalp health agent.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

While the specification concludes with claims particularly pointing out and distinctly claiming the invention, it is believed that the present invention will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

The term "coacervate" as used herein, means the complex which forms between surfactant and polymer that may either be soluble or insoluble in the neat composition, typically forming an insoluble complex in the neat composition, and which may become less soluble upon dilution and thus yielding an increase in its level of phase separation or precipitate in solution.

The term "floc" as used herein, means localized clusters of agglomerated, insoluble coacervate, which may comprise polymer, surfactant, water and dispersed phases present in the composition such as scalp health agent and silicone emulsion. Any floc size disclosed herein is obtained using the Lasentec FBRM Method, which is described below.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the hair care composition.

As used herein, "personal care compositions" includes products such as shampoos, shower gels, liquid hand cleansers, hair colorants, facial cleansers, and other surfactant-based liquid compositions As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Scalp Health Agent

Scalp Health agents may be surfactant soluble or particulates. Surfactant soluble scalp health agent may be one material or a mixture selected from the groups consisting of: azoles, such as climbazole, ketoconazole, itraconazole, econazole, and elubiol; hydroxy pyridones, such as octopirox (piroctone olamine), ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. In an embodiment, the azole anti-microbial agent is ketoconazole. In an embodiment, the sole anti-microbial agent is ketoconazole.

The compositions of the present invention may also contain a scalp health agent particulates. Suitable, non-limiting examples of scalp health agent particulates include: pyridinethione salts, selenium sulfide, particulate sulfur, and mixtures thereof. Such scalp health agent particulate should be physically and chemically compatible with the essential components of the composition, and should not otherwise unduly impair product stability, aesthetics or performance.

1. Pyridinethione Salts

Pyridinethione scalp health agent particulates, especially 1-hydroxy-2-pyridinethione salts, are one embodiment of a particulate scalp health agent for use in compositions of the present invention. The concentration of pyridinethione scalp health agent particulate typically ranges from about 0.1% to about 10%, by weight of the composition. In an embodiment of the present invention, pyridinethione salts include those formed from heavy metals such as zinc, copper, tin, cadmium, magnesium, aluminum and zirconium. In an embodiment of the present invention, a pyridinethione salts formed from a heavy metal zinc, and in a further embodiment, the zinc salt of 1-hydroxy-2-pyridinethione (known as "zinc pyridinethione" or "ZPT"), and yet a further embodiment of 1-hydroxy-2-pyridinethione salts in platelet particle form, wherein the particles have an average size of up to about 20μ. In an embodiment of the present invention, the particles have an average size up to about 5μ, and in a further embodiment up to about 2.5μ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the scalp health agent particulate in the compositions herein, that the growth or re-growth of hair may be stimulated or regulated, or both, or that hair loss may be reduced or inhibited, or that hair may appear thicker or fuller.

2. Other Anti-Microbial Actives

In addition to the scalp health agent selected from polyvalent metal salts of pyrithione, the present invention may further comprise one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. In an embodiment of the present invention, anti-microbials include itraconazole, ketoconazole, selenium sulphide and coal tar.

b. Selenium Sulfide

Selenium sulfide is a particulate scalp health agent suitable for use in the anti-microbial compositions of the present invention. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 μm, as measured by forward laser light scattering device (e.g. Malvern 3600 instrument), and in an embodiment of the present invention, less than 10 μm. Selenium sulfide compounds are described, for example, in U.S. Pat. Nos. 2,694,668; 3,152,046; 4,089,945; and 4,885,107.

c. Sulfur

Sulfur may also be used as a particulate anti-microbial/scalp health agent in the anti-microbial compositions of the present invention.

d. Keratolytic Agents

The present invention may further comprise one or more keratolytic agents such as Salicylic Acid.

The present invention may also comprise a combination of surfactant soluble anti-scalp health agents and particulate scalp health agents. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

e. Additional Anti-Microbial Actives

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbazole combinations, and salicylic acid and octopirox combinations, zinc pyrithione and climbazole and mixtures thereof.

In an embodiment, the scalp health agent may be present in an amount from about 0.01% to 10%, in a further embodiment from about 0.1% to 9%, in a further embodiment from about 0.25% to 8%, in yet a further embodiment from about 0.5% to 6%.

In an embodiment, the composition comprises an effective amount of a zinc-containing layered material. Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1+x}M^{2+}_{1+x}(OH)_{3(1-y)}]^+ A^{n-}_{(1-3y)/n} \cdot nH_2O$ where the two metal ions ($M^{2+}$) may be the same or different. If they are the same and represented by zinc, the formula simplifies to $[Zn_{1+x}(OH)_2]^{2x+}2xA^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

A. Detersive Surfactant

The hair care composition may comprise greater than about 14% by weight of a surfactant system which provides cleaning performance to the composition, in an embodiment greater than 20% by weight of a surfactant system which provides cleaning performance to the composition. The surfactant system comprises an anionic surfactant and/or a combination of anionic surfactants and/or a combination of anionic surfactants and co-surfactants selected from the group consisting of amphoteric, zwitterionic, nonionic and mixtures thereof. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety.

In an embodiment, the hair care composition may comprise from about 10% to about 25%, from about 11% to about 20%, from about 12% to about 20%, and/or from about 12% to about 18% by weight of one or more surfactants.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the hair care composition include ammonium lauryl sulfate, ammonium laureth sulfate, ammonium C10-15 pareth sulfate, ammonium C10-15 alkyl sulfate, ammonium C11-15 alkyl sulfate, ammonium decyl sulfate, ammonium deceth sulfate, ammonium undecyl sulfate, ammonium undeceth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium C10-15 pareth sulfate, sodium C10-15 alkyl sulfate, sodium C11-15 alkyl sulfate, sodium decyl sulfate, sodium deceth sulfate, sodium undecyl sulfate, sodium undeceth sulfate, potassium lauryl sulfate, potassium laureth sulfate, potassium C10-15 pareth sulfate, potassium C10-15 alkyl sulfate, potassium C11-15 alkyl sulfate, potassium decyl sulfate, potassium deceth sulfate, potassium undecyl sulfate, potassium undeceth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

The composition of the present invention can also include anionic surfactants selected from the group consisting of:
a) $R_1O(CH_2CHR_3O)_ySO_3M$;
b) $CH_3(CH_2)_zCHR_2CH_2O(CH_2CHR_3O)_ySO_3M$; and
c) mixtures thereof,
where $R_1$ represents $CH_3(CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not zero (0), and M is a monovalent or divalent, positively-charged cation.

Suitable anionic alkyl sulfates and alkyl ether sulfate surfactants include, but are not limited to, those having branched alkyl chains which are synthesized from C8 to C18 branched alcohols which may be selected from the group consisting of: Guerbet alcohols, aldol condensation derived alcohols, oxo alcohols, F-T oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISOFOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfate and sodium trideceth-3 sulfate. The composition of the present invention can also include sodium tridecyl sulfate.

The composition of the present invention can also include anionic alkyl and alkyl ether sulfosuccinates and/or dialkyl and dialkyl ether sulfosuccinates and mixtures thereof. The dialkyl and dialkyl ether sulfosuccinates may be a C6-15 linear or branched dialkyl or dialkyl ether sulfosuccinate. The alkyl moieties may be symmetrical (i.e., the same alkyl moieties) or asymmetrical (i.e., different alkyl moieties). Nonlimiting examples include: disodium lauryl sulfosuccinate, disodium laureth sulfosuccinate, sodium bistridecyl sulfosuccinate, sodium dioctyl sulfosuccinate, sodium dihexyl sulfosuccinate, sodium dicyclohexyl sulfosuccinate, sodium diamyl sulfosuccinate, sodium diisobutyl sulfosuccinate, linear bis(tridecyl) sulfosuccinate and mixtures thereof.

The hair care composition may comprise a co-surfactant. The co-surfactant can be selected from the group consisting of amphoteric surfactant, zwitterionic surfactant, non-ionic surfactant and mixtures thereof. The co-surfactant can include, but is not limited to, lauramidopropyl betaine, cocoamidopropyl betaine, lauryl hydroxysultaine, sodium lauroamphoacetate, disodium cocoamphodiacetate, cocamide monoethanolamide and mixtures thereof.

The hair care composition may further comprise from about 0.25% to about 15%, from about 1% to about 14%, from about 2% to about 13% by weight of one or more amphoteric, zwitterionic, nonionic co-surfactants, or a mixture thereof.

Suitable amphoteric or zwitterionic surfactants for use in the hair care composition herein include those which are known for use in shampoo or other hair care cleansing. Non limiting examples of suitable zwitterionic or amphoteric surfactants are described in U.S. Pat. Nos. 5,104,646 and 5,106,609, which are incorporated herein by reference in their entirety.

Amphoteric co-surfactants suitable for use in the composition include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, thoseselected from the group consisting of: sodium cocaminopropionate, sodium cocaminodipropionate, sodium cocoamphoacetate, sodium cocoamphodiacetate, sodium cocoamphohydroxypropylsulfonate, sodium cocoamphopropionate, sodium cornamphopropionate, sodium lauraminopropionate, sodium lauroamphoacetate, sodium lauroamphodiacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphodiacetate, ammonium cocoamphohydroxypropylsulfonate, ammonium cocoamphopropionate, ammonium cornamphopropionate, ammonium lauraminopropionate, ammonium lauroamphoacetate, ammonium lauroamphodiacetate, ammonium lauroamphohydroxypropylsulfonate, ammonium lauroamphopropionate, ammonium cornamphopropionate, ammonium lauriminodipropionate, triethanolamine cocaminopropionate, triethanolamine cocaminodipropionate, triethanolamine cocoamphoacetate, triethanolamine cocoamphohydroxypropylsulfonate, triethanolamine cocoamphopropionate, triethanolamine cornamphopropionate, triethanolamine lauraminopropionate, triethanolamine lauroamphoacetate, triethanolamine lauroamphohydroxypropylsulfonate, triethanolamine lauroamphopropionate, triethanolamine cornamphopropionate, triethanolamine lauriminodipropionate, cocoamphodipropionic acid, disodium caproamphodiacetate, disodium caproamphoadipropionate, disodium caproamphodiacetate, disodium caproamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof The composition may comprises a zwitterionic co-surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof.

Suitable nonionic surfactants for use in the present invention include those described in McCutcheion's Detergents and Emulsifiers, North American edition (1986), Allured Publishing Corp., and McCutcheion's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

The co-surfactant can be a non-ionic surfactant selected from the alkanolamides group including: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, PPG-2 Hydroxyethyl Isostearamide and mixtures thereof.

Representative polyoxyethylenated alcohols include alkyl chains ranging in the C9-C16 range and having from about 1 to about 110 alkoxy groups including, but not limited to, laureth-3, laureth-23, ceteth-10, steareth-10, steareth-100, beheneth-10, and commercially available from Shell Chemicals, Houston, Tex. under the trade names Neodol® 91, Neodol® 23, Neodol® 25, Neodol® 45, Neodol® 135, Neodol® 1 67, Neodol® PC 100, Neodol® PC 200, Neodol® PC 600, and mixtures thereof.

Also available commercially are the polyoxyethylene fatty ethers available commercially under the Brij® trade name from Uniqema, Wilmington, Del., including, but not limited to, Brij® 30, Brij® 35, Brij® 52, Brij® 56, Brij® 58, Brij® 72, Brij® 76, Brij® 78, Brij® 93, Brij® 97, Brij® 98, Brij® 721 and mixtures thereof.

Suitable alkyl glycosides and alkyl polyglucosides can be represented by the formula (S)n-O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, lauryl alcohol, myristyl alcohol, cetyl alcohol, stearyl alcohol, oleyl alcohol, and the like. Examples of these surfactants include alkyl polyglucosides wherein S is a glucose moiety, R is a C8-20 alkyl group, and n is an integer of from about 1 to about 9. Commercially available examples of these surfactants include decyl polyglucoside and lauryl polyglucoside available under trade names APG® 325 CS, APG® 600 CS and APG® 625 CS) from Cognis, Ambler, Pa. Also useful herein are sucrose ester surfactants such as sucrose cocoate and sucrose laurate and alkyl polyglucosides available under trade names Triton™ BG-10 and Triton™ CG-110 from The Dow Chemical Company, Houston, Tex.

Other nonionic surfactants suitable for use in the present invention are glyceryl esters and polyglyceryl esters, including but not limited to, glyceryl monoesters, glyceryl monoesters of C12-22 saturated, unsaturated and branched chain fatty acids such as glyceryl oleate, glyceryl monostearate, glyceryl monopalmitate, glyceryl monobehenate, and mixtures thereof, and polyglyceryl esters of C12-22 saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof.

Also useful herein as nonionic surfactants are sorbitan esters. Sorbitan esters of C12-22 saturated, unsaturated, and branched chain fatty acids are useful herein. These sorbitan esters usually comprise mixtures of mono-, di-, tri-, etc. esters. Representative examples of suitable sorbitan esters include sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), and sorbitan isostearate.

Also suitable for use herein are alkoxylated derivatives of sorbitan esters including, but not limited to, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), and mixtures thereof, all available from Uniqema.

Also suitable for use herein are alkylphenol ethoxylates including, but not limited to, nonylphenol ethoxylates (Tergitol™ NP-4, NP-6, NP-7, NP-8, NP-9, NP-10, NP-11, NP-12, NP-13, NP-15, NP-30, NP-40, NP-50, NP-55, NP-70 available from The Dow Chemical Company, Houston, Tex.) and octylphenol ethoxylates (Triton™ X-15, X-35, X-45, X-114, X-100, X-102, X-165, X-305, X-405, X-705 available from The Dow Chemical Company, Houston, Tx).

Also suitable for use herein are tertiary alkylamine oxides including lauramine oxide and cocamine oxide.

Non limiting examples of other anionic, zwitterionic, amphoteric, and non-ionic additional surfactants suitable for use in the hair care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Suitable surfactant combinations comprise an average weight % of alkyl branching of from about 0.5% to about 30%, alternatively from about 1% to about 25%, alternatively from about 2% to about 20%. The surfactant combination can have a cumulative average weight % of C8 to C12 alkyl chain lengths of from about 7.5% to about 25%, alternatively from about 10% to about 22.5%, alternatively from about 10% to about 20%. The surfactant combination can have an average C8-C12/C13-C18 alkyl chain ratio from about 3 to about 200, alternatively from about 25 to about 175.5, alternatively from about 50 to about 150, alternatively from about 75 to about 125.

B. Cationic Polymers

The hair care composition also comprises a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The hair care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

According to one embodiment, the cationic polymer, including but not limited to a cationic guar polymer, has a weight average Molecular weight of less than 2.2 million g/mol, or from about 150 thousand to about 2.2 million g/mol, or from about 200 thousand to about 2.2 million g/mol, or from about 300 thousand to about 1.2 million g/mol, or from about 750,000 thousand to about 1 million g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.8 meq/g.

According to one embodiment, the cationic guar polymer has a weight average Molecular weight of less than about 1.5 million g/mol, and has a charge density of from about 0.1 meq/g to about 2.5 meq/g. In an embodiment, the cationic guar polymer has a weight average molecular weight of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The cationic guar polymer may be formed from quaternary ammonium compounds. In an embodiment, the quaternary ammonium compounds for forming the cationic guar polymer conform to the general formula 1:

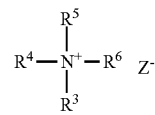

wherein where $R^3$, $R^4$ and $R^5$ are methyl or ethyl groups; $R^6$ is either an epoxyalkyl group of the general formula 2:

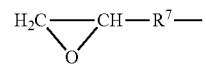

or $R^6$ is a halohydrin group of the general formula 3:

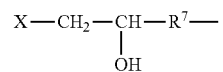

wherein $R^7$ is a $C_1$ to $C_3$ alkylene; X is chlorine or bromine, and Z is an anion such as Cl-, Br-, I- or $HSO_4$-.

In an embodiment, the cationic guar polymer conforms to the general formula 4:

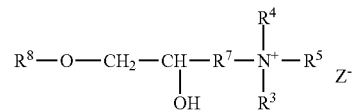

wherein $R^8$ is guar gum; and wherein $R^4$, $R^5$, $R^6$ and $R^7$ are as defined above; and wherein Z is a halogen. In an embodiment, the cationic guar polymer conforms to Formula 5:

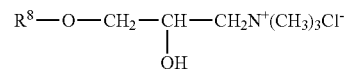

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Solvay, for example Jaguar® C-500, commercially available from Solvay. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.3 meq/g and a molecular weight of about 500,000 g/mol and is available from Solvay as Jaguar® Optima. Other suitable guar hydroxypropyltrimonium chloride are: guar hydroxypropyltrimonium chloride which has a charge density of about 0.7 meq/g and a molecular weight of about 1,500,000 g/mol and is available from Solvay as Jaguar® Excel. Other suitable guar hydroxypropyltrimonium chloride are: guar hydroxypropyltrimonium chloride which has a charge density of about 1.1 meq/g and a molecular weight of about 500,000 g/mol and is available from ASI, a charge density of about 1.5 meq/g and a molecular weight of about 500,000 g/mole is available from ASI. Other suitable guar hydroxypropyltrimonium chloride are: Hi-Care 1000, which has a charge density of about 0.7 meq/g and a Molecular weight of about 600,000 g/mole and is available from Solvay; N-Hance 3269 and N-Hance 3270, which have a charge density of about 0.7 meq/g and a molecular weight of about 425,000 g/mol and are available from ASI; N-Hance 3196, which has a charge density of about 0.8 meq/g and a molecular weight of about 1,100,000 g/mol and is available from ASI. AquaCat CG518 has a charge density of about 0.9 meq/g and a Molecular weight of about 50,000 g/mol and is available from ASI. BF-13, which is a borate (boron) free guar of charge density of about 1.1 meq/g and molecular weight of about 800,000 and BF-17, which is a borate (boron) free guar of charge density of about 1.7 meq/g and M. Wt. of about 800,000 both available from ASI.

The hair care compositions of the present invention may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

In one embodiment of the invention, the non-guar galactomannan polymer derivatives have a M. Wt. from about 1,000 to about 10,000,000, and/or from about 5,000 to about 3,000,000.

The hair care compositions of the invention can also include galactomannan polymer derivatives which have a cationic charge density from about 0.5 meq/g to about 7 meq/g. In one embodiment of the present invention, the galactomannan polymer derivatives have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

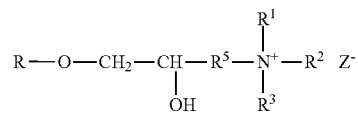

wherein R is the gum. The cationic galactomannan derivative can be a gum hydroxypropyltrimethylammonium chloride, which can be more specifically represented by the general formula 7:

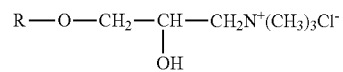

Alternatively the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 1,000 g/mol to about 10,000,000 g/mol, and/or from about 50,000 g/mol to about 1,000,000 g/mol, and/or from about 100,000 g/mol to about 900,000 g/mol, and/or from about 150,000 g/mol to about 400,000 g/mol and a cationic charge density from about 1 meq/g to about 5 meq/g, and/or from 2 meq/g to about 4 meq/g and can be derived from a *cassia* plant.

The hair care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cationically modified starch polymers disclosed herein have a percent of bound nitrogen of from about 0.5% to about 4%.

The cationically modified starch polymers for use in the hair care compositions can have a molecular weight about 850,000 g/mol to about 1,500,000 g/mol and/or from about 900,000 g/mol to about 1,500,000 g/mol.

The hair care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance of about 80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in hair care compositions are available from known starch suppliers. Also suitable for use in hair care compositions are nonionic modified starch that can be further derivatized to a cationically modified starch as is known in the art. Other suitable modified starch starting materials may be quaternized, as is known in the art, to produce the cationically modified starch polymer suitable for use in hair care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The hair care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:

(i) an acrylamide monomer of the following Formula AM:

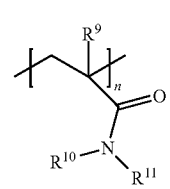

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$ cycloalkyl; and (ii) a cationic monomer conforming to Formula CM:

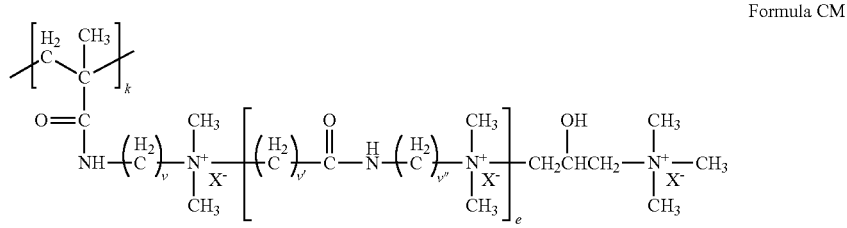

Formula CM where k=1, each of v, v', and v" is independently an integer of from 1 to 6, w is zero or an integer of from 1 to 10, and X⁻ is an anion.

The cationic monomer can conform to Formula CM and where k=1, v=3 and w=0, z=1 and X⁻ is Cl⁻ to form the following structure:

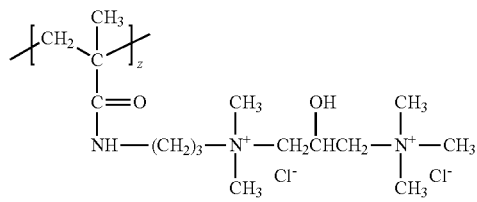

The above structure may be referred to as diquat. Alternatively, the cationic monomer can conform to Formula CM and wherein v and v" are each 3, v'=1, w=1, y=1 and X⁻ is Cl⁻, such as:

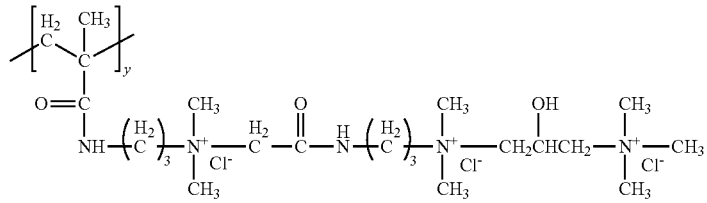

The above structure may be referred to as triquat.

Suitable acrylamide monomer include, but are not limited to, either acrylamide or methacrylamide.

The cationic copolymer (b) can be AM:TRIQUAT which is a copolymer of acrylamide and 1,3-Propanediaminium, N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT may have a charge density of 1.6 meq/g and a molecular weight of 1.1 million g/mol.

In an alternative embodiment, the cationic copolymer is of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth) acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth) acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth) acrylate, diethylaminomethyl (meth)acrylate, diethylaminoethyl (meth)acrylate; and diethylaminopropyl (meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). the cationic monomer when based on (meth)acrylamides can be quaternized dialkylaminoalkyl (meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 100 thousand g/mol to about 1.5 million g/mol, or from about 300 thousand g/mol to about 1.5 million g/mol, or from about 500 thousand g/mol to about 1.5 million g/mol, or from about 700 thousand g/mol to about 1.0 million g/mol, or from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC may have a charge density of about 1.3 meq/g and a molecular weight of about 1.1 million g/mol. The cationic copolymer can be AM:ATPAC. AM:ATPAC can have a charge density of about 1.8 meq/g and a molecular weight of about 1.1 million g/mol.

(a) Cationic Synthetic Polymers

The hair care composition can comprise a cationic synthetic polymer that may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

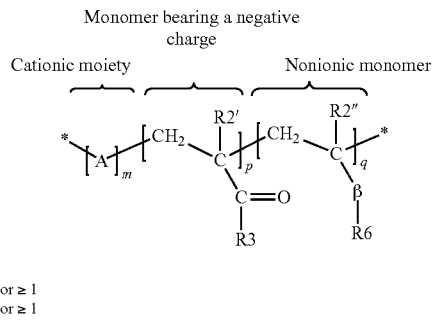

$m \geq 1$
$p = 0$ or $\geq 1$
$q = 0$ or $\geq 1$
$m \geq p$ where A, may be one or more of the following cationic moieties:

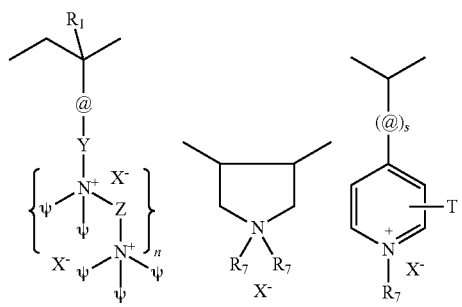

where @=amido, alkylamido, ester, ether, alkyl or alkylaryl;

where Y=C1-C22 alkyl, alkoxy, alkylidene, alkyl or aryloxy;

where ψ=C1-C22 alkyl, alkyloxy, alkyl aryl or alkyl arylox;

where Z=C1-C22 alkyl, alkyloxy, aryl or aryloxy;

where R1=H, C1-C4 linear or branched alkyl;

where s=0 or 1, n=0 or ≥1;

where T and R7=C1-C22 alkyl; and where X−=halogen, hydroxide, alkoxide, sulfate or alkylsulfate.

Where the monomer bearing a negative charge is defined by R2'=H, C1-C4 linear or branched alkyl and R3 as:

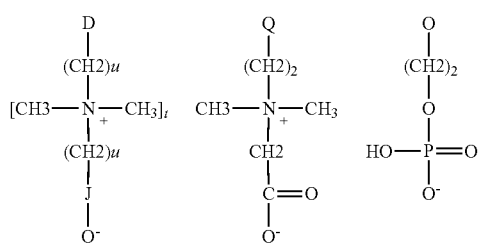

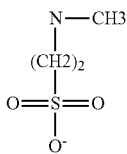

-continued where D=O, N, or S;
where Q=NH$_2$ or O;
where u=1-6;
where t=0-1; and
where J=oxygenated functional group containing the following elements P, S, C.

Where the nonionic monomer is defined by R2″=H, C1-C4 linear or branched alkyl, R6=linear or branched alkyl, alkyl aryl, aryl oxy, alkyloxy, alkylaryl oxy and β is defined as

and
where G' and G″ are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X−) in association with the synthetic cationic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics. Non limiting examples of such counterions include halides (e.g., chlorine, fluorine, bromine, iodine), sulfate and methylsulfate.

The cationic polymer described herein can aid in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the hair care composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable hair care composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. In some embodiments, the cationic charge density is about 6.2 meq/gm. The polymers also have a M. Wt. of from about 1,000 to about 5,000,000, and/or from about 10,000 to about 1,500,000, and/or from about 100,000 to about 1,500,000.

In another embodiment of the invention cationic synthetic polymers that provide enhanced conditioning and deposition of benefit agents but do not necessarily form lyotropic liquid crystals have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M. Wt. of from about 1,000 to about 1,500,000, from about 10,000 to about 1,500,000, and from about 100,000 to about 1,500,000.

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Non-limiting examples include: JR-30M, KG-30M, JP, LR-400 and mixtures thereof. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

The concentration of the cationic polymers ranges about 0.01% to about 5%, from about 0.08% to about 3%, from about 0.1% to about 2%, and/or from about 0.2% to about 1%, by weight of the hair care composition.

Gel Network

In an embodiment of the present invention, a gel network may be present. The gel network component of the present invention comprises at least one fatty amphiphile. As used herein, "fatty amphiphile" refers to a compound having a hydrophobic tail group as defined as an alkyl, alkenyl (containing up to 3 double bonds), alkyl aromatic, or branched alkyl group of $C_{12}$-$C_{70}$ length and a hydrophilic head group which does not make the compound water soluble, wherein the compound also has a net neutral charge at the pH of the shampoo composition.

The shampoo compositions of the present invention comprise fatty amphiphile as part of the pre-formed dispersed gel network phase in an amount from about 0.05% to about 14%, preferably from about 0.5% to about 10%, and more preferably from about 1% to about 8%, by weight of the shampoo composition.

According to the present invention, suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741> "Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point for use in the present invention. A mixture of two or more fatty amphiphiles, wherein the mixture comprises at least one fatty amphiphile having an individual melting point of less than about 27° C., still is suitable for use in the present invention provided that the composite melting point of the mixture is at least about 27° C.

Suitable fatty amphiphiles of the present invention include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, and phospholipids and mixtures thereof.

In a further embodiment of the present invention, the shampoo composition may comprise fatty alcohol gel networks. These gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

The fatty alcohol can be included in the fatty alcohol gel network at a level by weight of from about 0.05 wt % to about 14 wt %. For example, the fatty alcohol may be present in an amount ranging from about 1 wt % to about 10 wt %, and/or from about 6 wt % to about 8 wt %.

The fatty alcohols useful herein include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 1 provides the components and their respective amounts for an example gel network composition.

TABLE 1

Gel network components

| Ingredient | Wt. % |
|---|---|
| Water | 78.27% |
| Cetyl Alcohol | 4.18% |
| Stearyl Alcohol | 7.52% |
| Sodium laureth-3 sulfate (28% Active) | 10.00% |
| 5-Chloro-2-methyl-4-isothiazolin-3-one, Kathon CG | 0.03% |

1. Water Miscible Solvents

The carrier useful in embodiments of the hair care composition includes water and water solutions of lower alkyl alcohols, polyhydric alcohols, ketones having from 3 to 4 carbons atoms, C1-C6 esters of C1-C6 alcohols, sulfoxides, amides, carbonate esters, ethoxylated and proposylated C1-C10 alcohols, lactones, pyrollidones, and mixtures thereof. Non-limited lower alkyl alcohol examples are monohydric alcohols having 1 to 6 carbons, such as ethanol and isopropanol. Non-limiting examples of polyhydric alcohols useful herein include propylene glycol, dipropylene glycol, butylenes glycol, hexylene glycol, glycerin, propane diol and mixtures thereof.

In an embodiment of the present invention, the hair care composition may comprise a hydrotrope/viscosity modifier which is an alkali metal or ammonium salt of a lower alkyl benzene sulphonate such as sodium xylene sulphonate, sodium cumene sulphonate or sodium toluene sulphonate.

In a further embodiment of the present invention, the hair care composition may comprise silicone/PEG-8 silicone/PEG-9 silicone/PEG-n silicone/silicone ether (n could be another integer), non-limiting examples include PEGS-dimethicone A208) MW 855, PEG 8 Dimethicone D208 MW 2706.

C. Propellant or Blowing Agent

The hair care composition described herein may comprise from about from about 1% to about 10% propellant or blowing agent, alternatively from about 2% to about 8% propellant, by weight of the hair care composition.

The propellant or blowing agent may comprise one or more volatile materials, which in a gaseous state, may carry the other components of the hair care composition in particulate or droplet form or as a foam. The propellant or blowing agent may have a boiling point within the range of from about −45° C. to about 5° C. The propellant or blowing agent may be liquefied when packaged in convention aerosol containers under pressure. The rapid boiling of the propellant or blowing agent upon leaving the aerosol foam dispenser may aid in the atomization or foaming of the other components of the hair care composition.

Aerosol propellants or blowing agents which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoro ethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant or blowing agent may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar.

D. Additional Scalp Health Agents

In an embodiment of the present invention, one or more scalp health agent may be added to provide scalp benefits in addition to the anti-fungal/scalp health efficacy provided by the surfactant soluble scalp health agents. This group of materials is varied and provides a wide range of benefits including moisturization, barrier improvement, anti-fungal, anti-microbial and anti-oxidant, anti-itch, and sensates, and additional scalp health agents. Such scalp health agents include but are not limited to: vitamin E and F, salicylic acid, niacinamide, caffeine, panthenol, zinc oxide, zinc carbonate, glycols, glycolic acid, PCA, PEGs, erythritol, glycerin, triclosan, lactates, hyaluronates, allantoin and other ureas, betaines, sorbitol, glutamates, xylitols, menthol, menthyl lactate, iso cyclomone, benzyl alcohol, a compound comprising the following structure:

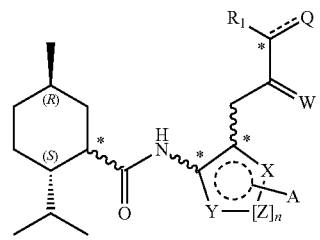

$R_1$ is selected from H, alkyl, amino alkyl, alkoxy;
Q=$H_2$, O, —$OR_1$, —$N(R_1)_2$, —$OPO(OR_1)_x$, —$PO(OR_1)_x$, —$P(OR_1)_x$ where x=1-2;
V=$NR_1$, O, —$OPO(OR_1)_x$, —$PO(OR_1)_x$, —$P(OR_1)_x$ where x=1-2;
W=$H_2$, O;
X, Y=independently selected from H, aryl, naphthyl for n=0;
X, Y=aliphatic $CH_2$ or aromatic CH for n≥1 and Z is selected from aliphatic $CH_2$, aromatic CH, or heteroatom;
A=lower alkoxy, lower alkylthio, aryl, substituted aryl or fused aryl; and stereochemistry is variable at the positions marked*.

and natural extracts/oils including peppermint, spearmint, argan, jojoba and aloe.

E. Optional Ingredients

In accordance with embodiments of the present invention, the hair care composition may further comprise one or more optional ingredients, including benefit agents Suitable benefit agents include, but are not limited to conditioning agents, cationic polymers silicone emulsions, scalp health agents, gel networks, chelating agents, and, natural oils such as sun flower oil or castor oil. Additional suitable optional ingredients include but are not limited to perfumes, perfume microcapsules, colorants, particles, anti-microbials, foam busters, anti-static agents, anionic polymers, rheology modifiers and thickeners, thickener polymers, suspension materials and structurants, pH adjusting agents and buffers, preservatives, pearlescent agents, solvents, diluents, anti-oxidants, vitamins and combinations thereof. In an embodiment of the present invention, the composition may have from about 0.5% to about 7% of a perfume.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

1. Conditioning Agents

The conditioning agent of the hair care compositions can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference.

The silicone conditioning agents for use in the compositions of the present invention can have a viscosity, as measured at 25° C., from about 20 to about 2,000,000 centistokes ("csk"), from about 1,000 to about 1,800,000 csk, from about 10,000 to about 1,500,000 csk, and/or from about 20,000 to about 1,500,000 csk.

The dispersed silicone conditioning agent particles typically have a volume average particle diameter ranging from about 0.01 micrometer to about 60 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the embodiments of the present invention include, but are not limited to, emulsions of insoluble polysiloxanes prepared in accordance with the descriptions provided in U.S. Pat. No. 6,316,541 or 4,476,282 or U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having an internal phase viscosity from about 5 csk to about 500,000 csk. For example, the insoluble polysiloxane may have an internal phase viscosity less 400,000 csk, preferably less than 200,000 csk, more preferably from about 10,000 csk to about 180,000 csk. The insoluble polysiloxane can have an average particle size within the range from about 10 nm to about 10 micron. The average particle size may be within the range from about 15 nm to about 5 micron, from about 20 nm to about 1 micron, or from about 25 nm to about 500 nm.

The average molecular weight of the insoluble polysiloxane, the internal phase viscosity of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

The conditioning agent of the hair care compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

2. Emusifiers

A variety of anionic and nonionic emulsifiers can be used in the hair care composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

3. Chelating Agents

The hair care composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Chelating agents can be incorporated in the compositions herein in amounts ranging from 0.001% to 10.0% by weight of the total composition, preferably 0.01% to 2.0%.

Nonlimiting chelating agent classes include carboxylic acids, aminocarboxylic acids, including aminocids, phosphoric acids, phosphonic acids, polyphosponic acids, polyethyleneimines, polyfunctionally-substituted aromatic, their derivatives and salts.

Nonlimiting chelating agents include the following materials and their salts. Ethylenediaminetetraacetic acid (EDTA), ethylenediaminetriacetic acid, ethylenediamine-N,N'-disuccinic acid (EDDS), ethylenediamine-N,N'-diglutaric acid (EDDG), salicylic acid, aspartic acid, glutamic acid, glycine, malonic acid, histidine, diethylenetriaminepentaacetate (DTPA), N-hydroxyethylethylenediaminetriacetate, nitrilotriacetate, ethylenediaminetetrapropionate, triethylenetetraaminehexaacetate, ethanoldiglycine, propylenediaminetetracetic acid (PDTA), methylglycinediacetic acid (MODA), diethylenetriaminepentaacetic acid, methylglycinediacetic acid (MGDA), N-acyl-N,N',N'-ethylenediaminetriacetic acid, nitrilotriacetic acid, ethylenediaminediglutaric acid (EDGA), 2-hydroxypropylenediamine disuccinic acid (HPDS), glycinamide-N, N'-disuccinic acid (GADS), 2-hydroxypropylenediamine-N—N'-disuccinic acid (HPDDS), N-2-hydroxyethyl-N,N-diacetic acid, glyceryliminodiacetic acid, iminodiacetic acid-N-2-hydroxypropyl sulfonic acid, aspartic acid N-carboxymethyl-N-2-hydroxypropyl-3-sulfonic acid, alanine-N,N'-diacetic acid, aspartic acid-N,N'-diacetic acid, aspartic acid N-monoacetic acid, iminodisuccinic acid, diamine-N,N'-dipolyacid, monoamide-N,N'-dipolyacid, diaminoalkyldi(sulfosuccinic acids) (DDS), ethylenediamine-N—N'-bis (ortho-hydroxyphenyl acetic acid)), N,N'-bis(2-hydroxybenzyl)ethylenediamine-N, N'-diacetic acid, ethylenediaminetetraproprionate, triethylenetetraaminehexacetate, diethylenetriaminepentaacetate, dipicolinic acid, ethylenedicysteic acid (EDC), ethylenediamine-N,N'-bis(2-hydroxyphenylacetic acid) (EDDHA), glutamic acid diacetic acid (GLDA), hexadentateaminocarboxylate (HBED), polyethyleneimine, 1-hydroxydiphosphonate, aminotri(methylenephosphonic acid) (ATMP), nitrilotrimethylenephosphonate (NTP), ethylenediaminetetramethylenephosphonate, diethylenetriaminepentamethylenephosphonate (DTPMP), ethane-1-hydroxydiphosphonate (HEDP), 2-phosphonobutane-1,2,4-tricarboxylic acid, polyphosphoric acid, sodium tripolyphosphate, tetrasodium diphosphate, hexametaphosphoric acid, sodium metaphosphate, phosphonic acid and derivatives, Aminoalkylen-poly (alkylenphosphonic acid), aminotri(1-ethylphosphonic acid), ethylenediaminetetra(1-ethylphosphonic acid), aminotri(1-propylphosphonic acid), aminotri(isopropylphosphonic acid), ethylenediaminetetra(methylenephosphonic acid) (EDTMP), 1,2-dihydroxy-3,5-disulfobenzene.

Aqueous Carrier

The hair care compositions can be in the form of pourable liquids (under ambient conditions). Such compositions will therefore typically comprise a carrier, which is present at a level of from about 40% to about 85%, alternatively from about 45% to about 80%, alternatively from about 50% to about 75% by weight of the hair care composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in embodiments of the hair care compositions of the present invention includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

The pH of the composition may be from about pH 3 to about pH 9, or in an embodiment from about pH 4 to about pH 8.5, or in a further embodiment from about pH 6.5-8.5.

G. Foam Dispenser

The hair care composition described herein may be provided in a foam dispenser. The foam dispenser may be an aerosol foam dispenser. The aerosol foam dispenser may comprise a reservoir for holding the hair treatment composition. The reservoir may be made out of any suitable material selected from the group consisting of plastic, metal, alloy, laminate, and combinations thereof. In an embodiment, the reservoir may be for one-time use. In an embodiment, the reservoir may be removable from the aerosol foam dispenser. Alternatively, the reservoir may be integrated with the aerosol foam dispenser. In an embodiment, there may be two or more reservoirs.

The foam dispenser may also be a mechanical foam dispenser. The mechanical foam dispenser described may be selected from the group consisting of squeeze foam dispensers, pump foam dispensers, other mechanical foam dispensers, and combinations thereof. In an embodiment, the mechanical foam dispenser is a squeeze foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The mechanical foam dispenser may comprise a reservoir for holding the hair treatment composition. The reservoir may be made out of any suitable material selected from the group consisting of plastic, metal, alloy, laminate, and combinations thereof. The reservoir may be a refillable reservoir such as a pour-in or screw-on reservoir, or the reservoir may be for one-time use. The reservoir may also be removable from the mechanical foam dispenser. Alternatively, the reservoir may be integrated with the mechanical foam dispenser. In an embodiment, there may be two or more reservoirs.

In an embodiment, the reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

H. Product Form

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the embodiments of the present invention may be hair tonics, leave-on hair products such as treatment, and styling products, rinse-off hair products such as shampoos and personal cleansing products, and treatment products; and any other form that may be applied to hair.

I. Applicator

In an embodiment of the present invention, the hair care composition may be dispensed from an applicator for dispensing directly to the scalp area. Dispensing directly onto the scalp via a targeted delivery applicator enables deposition of the non diluted cleaning agents directly where the cleaning needs are highest. This also minimizes the risk of eye contact with the cleansing solution.

The applicator is attached or can be attached to a bottle containing the cleansing hair care composition. The applicator can consist of a base that holds or extends to a single or plurality of tines. The tines have openings that may be at the tip, the base or at any point between the tip and the base. These openings allows for the product to be distributed from the bottle directly onto the hair and/or scalp.

Alternatively, the applicator can also consist of brush-like bristles attached or extending from a base. In this case product would dispense from the base and the bristles would allow for product distribution via the combing or brushing motion.

Applicator and tine design and materials can also be optimized to enable scalp massage. In this case it would be beneficial for the tine or bristle geometry at the tips to be more rounded similar to the roller ball applicator used for eye creams. It may also be beneficial for materials to be smoother and softer; for example metal or metal-like finishes, "rubbery materials".

Measurement of Scalp Health Agent Deposition

The on-scalp deposition of the scalp health agent is measured by having the hair of individuals washed with a composition comprising a scalp health agent, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of scalp health agent content by conventional methodology, such as HPLC. The percent agent deposited can be calculated using the following equation:

$$\% \text{ agent deposited} = \frac{\frac{\text{grams of agent deposited}}{\text{area of scalp extracted}}}{(\text{wt. \% agent in shampoo}) \times \frac{(\text{grams of shampoo applied})}{\text{area of scalp treated}}} \times 100\%$$

The deposition efficiency can be calculated using the following equation:

$$\text{Deposition efficiency} = \frac{\% \text{ agent deposited by example formula}}{\% \text{ agent deposited by control formula}}$$

Sample Calculation

Deposition amount: 1 ug/cm$^2$ (0.000001 g/cm$^2$)

Weight % of agent in product: 1.0% (0.01 gm of agent/gm of product)

Grams of product applied: 5.0 g

Area of Scalp Treated: 300 cm$^2$ for half head (figure based on average surface area of 600 cm$^2$ for whole head)

$$[1/\{(0.01\times5)/300\}]\times100=0.6\% \text{ of agent deposited}$$
Sample Calculation Equation:

The composition forms coacervate particles upon dilution of the composition with water. The percentage of coacervate particles with a floc size of greater than about 20 micron is from about 1% to about 60%. In an embodiment, the percentage of coacervate particles with a floc size of greater than about 20 micron is from about 1% to about 50%, or from about 1% to about 40%, or from about 1% to about 30%, or from about 5% to about 20% from about 5% to about 15%. The floc size is measured after diluting the composition 1:50 dilution with water.

The floc size may be measured using a Lasentec FBRM Method: In a suitable mixing vessel create a 1:9 dilution of composition in distilled water at ambient temperature and mix for 5 min at 250 rpm. Using a peristaltic pump transfer ambient distilled water into the mixing vessel at a rate of 100 g/min resulting in a final dilution of 1:50 parts composition to distilled water. After a 10 min equilibration period a Lasentec Focused Beam Reflectance Method (FBRM) [model S400A available from Mettler Toledo Corp] may be used to determine floc size and amount as measured by chord length and particle counts/sec (counts per sec).

Preparation of Shampoo Compositions

The shampoo compositions are prepared by adding surfactants, scalp health agents, perfume, viscosity modifiers, cationic polymers and the remainder of the water with ample agitation to ensure a homogenous mixture. The mixture can be heated to 50-75° C. to speed the solubilization of the soluble agents, then cooled. Product pH may be adjusted as necessary to provide shampoo compositions of the present invention which are suitable for application to human hair and scalp. and may vary from about pH 3 to 9, or from about pH 4 to 8.5, or from about pH 6.5 to 8.5 based on the selection of particular detersive surfactants and/or other components.

Non-Limiting Examples

The shampoo compositions illustrated in the following examples are prepared by conventional formulation and mixing methods. All exemplified amounts are listed as weight percents on an active basis and exclude minor materials such as diluents, preservatives, color solutions, imagery ingredients, botanicals, and so forth, unless otherwise specified. All percentages are based on weight unless otherwise specified.

|  | Example | | | | | | | | | | |
| --- | --- | --- | --- | --- | --- | --- | --- | --- | --- | --- | --- |
| Component | Comparative Example 1 | Comparative Example 2 | 3 | 4 | 5 | 6 | 7 | 8 | 9 | Comparative Example 10 | 11 |
| Guar hydroxypropyl trimonium chloride 1 | 0.3 | 0.3 | 0.3 | 0.3 | 0.3 | 0.3 | 0.25 | 0.3 | 0.3 | 0.3 | 0.3 |
| Acrylamide/Triquat 2 | — | — | — | — | — | — | — | — | — | 0.03 | 0.03 |
| Sodium laureth-1 sulfate 3 | 12 | 12 | 12 | 12 | 12 | 12.5 | 12 | 12 | 12 | 11.5 | 11.5 |
| Sodium Lauryl sulphate 4 | 0 | 0 | 0 | 0 | — | — | — | — | — | 1.5 | 1.5 |
| Cocamidopropyl betaine 5 | 1.5 | 1.5 | 1.5 | 1.5 | 1.5 | 1.5 | 1.5 | 1.25 | — | 1.25 | 1.25 |
| Cocamide MEA 6 | 1.5 | 1.5 | 1.5 | 1.5 | 1.5 | 1.5 | 1.5 | 1.5 | 1.5 | 2 | 2 |
| Dimethicone 7 | 0.8 | 2.7 | 2.7 | 0.8 | — | 0.8 | 0.85 | — | — | 0.8 | 0.8 |
| Dimethiconol 8 | — | — | — | — | 0.8 | — | — | — | 1 | — | — |
| Zinc Pyrithione 9 | 1 | 1 | 1 | 1 | 1 | 1 | 1 | 1 | 1 | 1 | 1 |
| Zinc Carbonate 10 | 1.61 | 1.61 | 1.61 | 1.61 | — | 1.61 | 1.61 | — | 1.61 | 1.61 | 1.61 |
| Stearyl Alcohol 11 | — | — | — | — | — | — | — | — | 1.29 | — | — |
| Cetyl Alcohol 12 | — | — | — | — | — | — | — | — | 0.71 | — | — |
| Glycol distearate 13 | 1.5 | 1.5 | 1.5 | 1.5 | 1.5 | 1.5 | 1.5 | 1.5 | 1.5 | 1.5 | 1.5 |
| Preservative 14 | 0.05 | 0.05 | 0.05 | 0.05 | 0.05 | 0.05 | 0.05 | 0.05 | 0.05 | 0.05 | 0.05 |
| Piroctone Olamine 15 | — | — | 1 | 1 | 0.5 | 1 | 1 | 1 | 1 | — | 1 |
| Caffeine 16 | 0.1 | 0.1 | 0.1 | 0.1 | — | 0.1 | 0.1 | — | 0.1 | — | — |
| Niacinamide 17 | 0.005 | 0.005 | 0.005 | 0.005 | — | — | — | — | 0.005 | — | — |
| Panthenol 18 | 0.005 | 0.005 | 0.005 | 0.005 | — | — | — | — | 0.005 | — | — |
| Polyquaternium-10 19 | 0.1 | 0.2 | 0.2 | 0.1 | 0.1 | 0.2 | 0.1 | 0.15 | 0.1 | — | — |
| Sodium Xylene Sulfonate 20 | QS | QS | QS | QS | QS | QS | QS | QS | QS | QS | QS |
| Fragrance | 0.9 | 0.9 | 0.9 | 0.9 | 0.9 | 0.9 | 0.9 | 0.9 | 0.9 | 0.8 | 0.8 |
| Hydrochloric Acid 6N | QS | QS | QS | QS | QS | QS | QS | QS | QS | QS | QS |
| Sodium Benzoate | 0.25 | 0.25 | 0.25 | 0.25 | 0.25 | 0.25 | 0.25 | 0.25 | 0.25 | 0.25 | 0.25 |
| Sodium Chloride | QS | QS | QS | QS | QS | QS | QS | QS | QS | QS | QS |
| Water | 78.38 | 76.38 | 75.38 | 77.38 | 79.6 | 76.79 | 77.39 | 80.1 | 76.68 | 77.41 | 76.41 |
| Total | 100 | 100 | 100 | 100 | 100 | 100 | 100 | 100 | 100 | 100 | 100 |

1. Jaguar C500 from Solvay with a M.Wt. of about 500,000 g/mol and charge density of about 0.8 meq/g.
2. Polyquaternium-76 (PQ-76) from Rhodia with a M.Wt. of about 1,000,000 g/mol and charge density of about 1.6 meq/g.
3. Sodium laureth-1 sulfate at 26% active from the Stepan Company
4. Sodium Lauryl sulfate at 29% active from the Stepan Company
5. Amphosol HCA at 30% active from the Stepan Company
6. Ninol COMF at 85% active from the Stepan Company
7. Viscasil 330M from Momentive Performance Materials with a viscosity of 330,000 cSt (centistokes) utilizing about an average 30 micron emulsion.
8. BELSIL DM 5500 from Wacker Silicones
9. ZPT from Arch Chemical
10. Zinc carbonate from the Bruggeman Group
11. CO-1895 from Procter & Gamble
12. CO-1695 from Procter & Gamble
13. EGDS from Golschmidt Chemical Company
14. Kathon CG from Akzo Nobel
15. Octopirox from Clairiant
16. BASF Beauty Care Solutions
17. Roche Vitamins Inc
18. DSM Nutritional Products (Ayrshire GB)
19. JR30M available from Dow/Amerchol - DO WE NEED OTHERS?
20. Stepanate SXS at 40% from Stepan Results
In-Vivo ZPT Scalp Deposition Results

|  | Comparison 1 | | Comparison 2 | | Comparison 3 | | Comparison 4** | | |
| --- | --- | --- | --- | --- | --- | --- | --- | --- | --- |
| Formula: | Example 1 | Example 4 | Example 2 | Example 3 | Example 10 | Example 11 | Example 1 | Example 4 | Example 6 |
| # of Panelists: | 50 | 50 | 50 | 50 | 50 | 50 | 46 | 46 | 48 |
| % Agent Deposited | 0.24 | 0.42 | 0.36 | 0.72 | 0.66 | 0.60 | 0.45 | 0.72 | 1.86 |
| Deposition Efficiency | 175.0% | | 200.0% | | 90.9% | | n/a | 160% | 413% |
| Statistically Significant* | Yes | | Yes | | No | | n/a | Yes | Yes |

*Significance based on P value < 0.1

**Comparison 4 represents two different in-vivo tests that used the same control product, test protocol, and analysis techniques. The value given for the Example 1 result is an average across those two tests (0.9 ug/cm$^2$ and 0.6 um/cm$^2$)

In an embodiment of the present invention, the on-scalp deposition of the particulate scalp health agent deposition efficiency is increased by about 50% compared to a control with no soluble scalp health agent. In a further embodiment, the on-scalp deposition of the particulate scalp health agent deposition efficiency is increased by about 75% compared to a control with no soluble scalp health agent. In yet a further embodiment, the on-scalp deposition of the particulate scalp health agent deposition efficiency is increased by about 90% compared to a control with no soluble scalp health agent. In yet a further embodiment, the on-scalp deposition of the particulate scalp health agent deposition efficiency is increased by about 100% compared to a control with no soluble scalp health agent. In yet a further embodiment, the on-scalp deposition of the particulate scalp health agent deposition efficiency is increased by greater than about 100% compared to a control with no soluble scalp health agent.

Coacervate Floc Size Results

| Formula | % Coacervate Particles with Floc Size > (20 um) |
|---|---|
| Example 1 | 11.7% |
| Example 4 | 15.7% |
| Example 6 | 31.0% |

In a further embodiment of the present invention, the percentage of coacervate particles with a floc size of 20 microns is at least about 15%. In a further embodiment of the invention, the percentage of coacervate particles with a floc size of 20 microns is at least about 25%.

As can be seen by the in-vivo ZPT deposition results table above, the presence of octopirox in formulas of particular surfactant composition shows a very significant influence on the amount of ZPT deposited onto the scalp after use. Furthermore, it can be observed that increases in the level of the chosen cellulosic cationic polymer can have a significant impact on not only the particulate deposition amount, which should be mentioned is to a level that is significantly higher than we would expect in formulations without the synergistic effect of the piroctone olamine inclusion, but also on the size of the coacervate floc produced upon dilution. This is of particular interest due to the fact that when diluted, formulas that have coacervate floc distributions of smaller size dilution are more effective at depositing particles onto the scalp surface instead of onto the hair which effectively acts a filter, preventing the larger floc from ever seeing the scalp's surface. This in turn leads to better spatial distribution of the deposited scalp health agents over the surface of the scalp driving higher efficacy from the formulation.

ADDITIONAL EXAMPLES/COMBINATIONS

A. A hair care composition comprising:
   a) from about 10% to about 25% of one or more surfactants;
   b) from about 0.01% to 10% of one or more particulate scalp health agents;
   c) from about 0.01% to 10% of one or more surfactant soluble scalp health agents;
   d) from about 0.01% to 5% of one or more cationic polymers selected from the group consisting of a cationic cellulose;
   e) from about 0.01% to 5% of one or more cationic polymers selected from group consisting of one or more cationic guar polymers;
   and wherein an on-scalp deposition of the particulate scalp health agent deposition efficiency is increased by about 50% compared to a control with no soluble scalp health agent.
B. A hair care composition according to Paragraph A, wherein the on-scalp deposition of the particulate scalp health agent deposition efficiency is increased by about 75% compared to a control with no soluble scalp health agent.
C. A hair care composition according to Paragraph A-B, wherein the on-scalp deposition of the particulate scalp health agent deposition efficiency is increased by about 90% compared to a control with no soluble scalp health agent.
D. A hair care composition according to Paragraph A-C, wherein the composition forms coacervate particles upon dilution of the composition with water.
E. A hair care composition according to Paragraph A-D, and wherein the percentage of coacervate particles with a floc size of 20 microns is at least about 15%.
F. A hair care composition according to Paragraph A-E, and wherein the percentage of coacervate particles with a floc size of 20 microns is at least about 25%.
G. A hair care composition according to Paragraph A-F, wherein the cationic polymer is selected from the group consisting of salts of hydroxyethyl cellulose reacted with trimethyl ammonium substituted epoxide, polymeric quaternary ammonium salts of hydroxyethyl cellulose reacted with lauryl dimethyl ammonium-substituted epoxide, polymeric quaternary ammonium salts of hydroxyethyl cellulose reacted with lauryl dimethyl ammonium-substituted epoxide and trimethyl ammonium substituted epoxide and mixtures thereof.
H. A hair care composition according to Paragraph A-G, wherein the cationic polymer is a salt of hydroxyethyl cellulose reacted with trimethyl ammonium substituted epoxide.
I. A hair care composition according to Paragraph A-H, wherein the cationic guar polymer is selected from the group consisting of cationic guar gum derivatives.
J. A hair care composition according to Paragraph A-I, wherein the cationic guar gum derivative is guar hydroxypropyltrimonium chloride.
K. A hair care composition according to Paragraph A-J, wherein the guar hydroxypropyltrimonium chloride. has a charge density of 0.8 meq/g and a molecular weight of 500,000 g/mol.
L. A hair care composition according to Paragraph A-K, wherein the guar hydroxypropyltrimonium chloride which has a charge density of about 1.3 meq/g and a molecular weight of about 500,000 g/mol
M. A hair care composition according to Paragraph A-L, wherein the guar hydroxypropyltrimonium chloride has a charge density of about 1.1 meq/g and a molecular weight of about 500,000 g/mol.
N. A hair care composition according to Paragraph A-M, wherein the guar hydroxypropyltrimonium chloride has a charge density of about 0.8 meq/g and a molecular weight of about 1,100,000 g/mol;
O. A hair care composition according to Paragraph A-N, wherein the guar hydroxypropyltrimonium chloride has a charge density of about 1.1 meq/g and molecular weight of about 800,000.
P. A hair care composition according to Paragraph A-O, wherein the guar hydroxypropyltrimonium chloride has a charge density of about 1.5 meq/g and M. Wt. of about 800,000.

Q. A hair care composition according to Paragraph A-P, wherein the one or more cationic polymers is from about 0.08% to about 3%.
R. A hair care composition according to Paragraph A-Q, wherein the one of more cationic polymers is from about 0.1% to about 2%.
S. A hair care composition according to Paragraph A-R, wherein the one of more cationic polymers is from about 0.2% to about 1%.
T. A hair care composition according to Paragraph A-S, wherein the surfactant is an anionic surfactant or combinations of anionic surfactants.
U. A hair care composition according to Paragraph A-T, further comprising from about 0.25% to about 15% of one or more amphoteric, nonionic or zwitterionic co-surfactants.
V. A hair care composition according to Paragraph A-U, wherein the co-surfactant is selected from the group consisting of lauramidopropyl betaine, cocoamidopropyl betaine, lauryl hydroxysultaine, sodium lauroamphoacetate, disodium cocoamphodiacetate, cocamide monoethanolamide and mixtures thereof.
W. A hair care composition according to Paragraph A-V, wherein the antidandruff/scalp benefit agent is a surfactant soluble agent.
X. A hair care composition according to Paragraph A-W wherein the surfactant soluble agent is a hydroxyl pyridone.
Y. A hair care composition according to Paragraph A-X, wherein the hydroxyl pyridone is piroctone olamine.
Z. A hair care composition according to Paragraph A-Y, wherein the surfactant soluble agent is an azole.
AA. A hair care composition according to Paragraph A-Z, wherein the azole is climbazole.
BB. A hair care composition according to Paragraph A-AA, wherein the antidandruff/scalp benefit agent is an insoluble particulate.
CC. A hair care composition according to Paragraph A-BB, wherein the insoluble particulate is a selected from the group consisting of pyridinethione salts, selenium sulfide, particulate sulfur, and mixtures thereof.
DD. A hair care composition according to Paragraph A-CC, wherein the insoluble particulate is polyvalent metal salts of pyrithione.
EE. A hair care composition according to Paragraph A-DD, wherein the insoluble particulate is zinc pyrithione.
FF. A hair care composition according to Paragraph A-EE, wherein the scalp health agent is from about 0.1% to 9%.
GG. A hair care composition according to Paragraph A-FF, wherein scalp health agent is from about 0.25% to 8%.
HH. A hair care composition according to Paragraph A-GG, wherein the composition further comprises a gel network.
II. A hair care composition according to Paragraph A-HH, wherein the composition further comprising a conditioning agent.
JJ. A hair care composition according to Paragraph A-II, wherein the conditioning agent is a silicone.
KK. A hair care composition according to Paragraph A-JJ, wherein the scalp health agent is salicylic acid.
LL. A hair care composition according to Paragraph A-KK, wherein the scalp health agent is menthol and/or menthyl lactate.
MM. A hair care composition according to Paragraph A-LL, further comprising from about 0.5% to about 7% of a perfume.
NN. A hair care composition according to Paragraph A-MM, wherein the hair care composition is dispensed as a foam.
OO. A hair care composition according to Paragraph A-NN, wherein the hair care composition is dispensed as an aerosol foam.
PP. A hair care composition according to Paragraph A-OO, wherein a propellant or a blowing agent to dispense the composition as an aerosol foam is a chemically inert hydrocarbon, a halogenated hydrocarbon, and mixtures thereof.
QQ. A hair care composition according to Paragraph A-PP, wherein the hair care composition is dispensed as a pumped foam.
RR. A hair care composition according to Paragraph A-QQ, wherein the hair care composition is applied using an applicator.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition comprising:
    a) from about 10% to about 25% of one or more surfactants;
    b) from about 0.01% to 10% of one or more particulate scalp health agents;
    c) from about 0.01% to 10% of one or more surfactant soluble scalp health agents;
    d) from about 0.01% to 5% of one or more cationic cellulose polymers;
    e) from about 0.01% to 5% of one or more cationic guar polymers;
    and wherein an on-scalp deposition of the particulate scalp health agent deposition efficiency is increased by about 50% compared to a control with no soluble scalp health agent wherein the composition forms coacervate particles upon dilution of the composition with water and wherein the percentage of coacervate particles with a floc size of 20 microns is at least about 15%.

2. The hair care composition according to claim 1 wherein the on-scalp deposition of the particulate scalp health agent deposition efficiency is increased by about 75% compared to a control with no soluble scalp health agent.

3. The hair care composition according to claim 1 wherein the on-scalp deposition of the particulate scalp health agent deposition efficiency is increased by about 90% compared to a control with no soluble scalp health agent.

4. The hair care composition according to claim 1 and wherein the percentage of coacervate particles with a floc size of 20 microns is at least about 25%.

5. The hair care composition according to claim 1 wherein the one or more cationic cellulose polymers is selected from the group consisting of salts of hydroxyethyl cellulose reacted with trimethyl ammonium substituted epoxide, polymeric quaternary ammonium salts of hydroxyethyl cellulose reacted with lauryl dimethyl ammonium-substituted epoxide, polymeric quaternary ammonium salts of hydroxyethyl cellulose reacted with lauryl dimethyl ammonium-substituted epoxide and trimethyl ammonium substituted epoxide and mixtures thereof.

6. The hair care composition according to claim 5 wherein the one or more cationic cellulose polymers is a salt of hydroxyethyl cellulose reacted with trimethyl ammonium substituted epoxide.

7. The hair care composition according to claim 1 where in the one or more cationic guar polymers is a cationic guar gum derivative.

8. The hair care composition according to claim 7, wherein the cationic guar gum derivative is guar hydroxypropyltrimonium chloride.

9. The hair care composition according to claim 8 wherein the guar hydroxypropyltrimonium chloride has a charge density of 0.8 meq/g and a molecular weight of 500,000 g/mol.

10. The hair care composition according to claim 8 wherein the guar hydroxypropyltrimonium chloride which has a charge density of about 1.3 meq/g and a molecular weight of about 500,000 g/mol.

11. The hair care composition according to claim 8 wherein the guar hydroxypropyltrimonium chloride has a charge density of about 1.1 meq/g and a molecular weight of about 500,000 g/mol.

12. The hair care composition according to claim 8 wherein the guar hydroxypropyltrimonium chloride has a charge density of about 0.8 meq/g and a molecular weight of about 1,100,000 g/mol.

13. The hair care composition according to claim 8 wherein the guar hydroxypropyltrimonium chloride has a charge density of about 1.1 meq/g and molecular weight of about 800,000.

14. The hair care composition according to claim 8 wherein the guar hydroxypropyltrimonium chloride has a charge density of about 1.5 meq/g and M. Wt. of about 800,000.

15. The hair care composition according to claim 1 wherein the one or more cationic cellulose polymers is present in the amount of 0.08% to about 3%.

16. The hair care composition according to claim 1 wherein the one of more cationic cellulose polymers is present in the amount of 0.1% to about 2%.

17. The hair care composition according to claim 1 wherein the one of more cationic cellulose polymers is present in the amount of 0.2% to about 1%.

18. The hair care composition according to claim 1 wherein the one or more surfactants is an anionic surfactant or combinations of anionic surfactants.

19. The hair care composition according to claim 1 further comprising from about 0.25% to about 15% of one or more amphoteric, nonionic or zwitterionic co-surfactants.

20. The hair care composition according to claim 19 wherein the one or more amphoteric, nonionic or zwitterionic co-surfactants is selected from the group consisting of lauramidopropyl betaine, cocoamidopropyl betaine, lauryl hydroxysultaine, sodium lauroamphoacetate, disodium cocoamphodiacetate, cocamide monoethanolamide and mixtures thereof.

21. The hair care composition according to claim 1 wherein the one or more surfactant soluble scalp health agents comprises antidandruff/scalp benefit agents.

22. The hair care composition according to claim 1 wherein the one or more surfactant soluble scalp health agents is a hydroxyl pyridone.

23. The hair care composition according to claim 22 wherein the hydroxyl pyridone is piroctone olamine.

24. The hair care composition according to claim 1 wherein the one or more surfactant soluble scalp health agents is an azole.

25. The hair care composition according to claim 24 wherein the azole is climbazole.

26. The hair care composition according to claim 21 wherein one or more surfactant soluble scalp health agents comprise the antidandruff/scalp benefit agent which is an insoluble particulate.

27. The hair care composition according to claim 26 wherein the insoluble particulate is a selected from the group consisting of pyridinethione salts, selenium sulfide, particulate sulfur, and mixtures thereof.

28. The hair care composition according to claim 27 wherein the insoluble particulate is polyvalent metal salts of pyrithione.

29. The hair care composition according to claim 28 wherein the insoluble particulate is zinc pyrithione.

30. The hair care composition according to claim 1 wherein the one or more surfactant soluble scalp health agents is present in the amount of 0.1% to 9%.

31. The hair care composition according to claim 1 wherein the one or more surfactant soluble scalp health agents is present in the amount of 0.25% to 8%.

32. The hair care composition according to claim 1 wherein the composition further comprises a gel network.

33. The hair care composition according to claim 1 wherein the composition further comprising a conditioning agent.

34. The hair care composition according to claim 33 wherein the conditioning agent is a silicone.

35. The hair care composition according to claim 1 wherein the one or more surfactant soluble scalp health agents is salicylic acid.

36. The hair care composition according to claim 1 wherein the one or more surfactant soluble scalp health agents is menthol and/or menthyl lactate.

37. The hair care composition according to claim 1 further comprising from about 0.5% to about 7% of a perfume.

38. The hair care composition according to claim 1 wherein the hair care composition is dispensed as a foam.

39. The hair care composition according to claim 38 wherein the hair care composition is dispensed as an aerosol foam.

40. The hair care composition according to claim 39 wherein a propellant or a blowing agent to dispense the composition as an aerosol foam is a chemically inert hydrocarbon, a halogenated hydrocarbon, or mixtures thereof.

41. The hair care composition according to claim 38, wherein the hair care composition is dispersed as a pump foam.

42. The hair care composition according to claim 1 wherein the one or more cationic guar polymers is present in the amount of 0.08% to about 3%.

43. The hair care composition according to claim 1 wherein the one of more cationic guar polymers is present in the amount of 0.1% to about 2%.

44. The hair care composition according to claim 1 wherein the one of more cationic guar polymers is present in the amount of 0.2% to about 1%.

* * * * *